United States Patent [19]
Suzuki et al.

[11] Patent Number: 4,834,740
[45] Date of Patent: May 30, 1989

[54] METHOD FOR MAKING WEARABLE ARTICLES

[75] Inventors: Migaku Suzuki, Kawanoe; Mitsuzo Ochi, Ehime; Takeshi Kudo, Kawanoe, all of Japan

[73] Assignee: Uni-Charm Corporation, Ehime, Japan

[21] Appl. No.: 112,114

[22] Filed: Oct. 26, 1987

[30] Foreign Application Priority Data

Oct. 24, 1986 [JP] Japan .................................. 61-253496
Aug. 20, 1987 [JP] Japan .................................. 62-207070

[51] Int. Cl.$^4$ ............................................. A61F 13/16
[52] U.S. Cl. ................................................. 604/385.2
[58] Field of Search .................... 604/385.1, 385.2, 393

[56] References Cited

U.S. PATENT DOCUMENTS 4,695,278 9/1987 Lawson ............................. 604/385.2
4,704,116 11/1987 Enloe ................................. 604/385.2

Primary Examiner—Carroll B. Dority, Jr.
Attorney, Agent, or Firm—Fred Philpitt

[57] ABSTRACT

Here is disclosed a method for making wearable articles such as disposable diaper, disposable diaper cover or the like, more particularly, a method for forming side flaps provided with elastic members to provide fitness around wearer's legs. According to this method, the side flaps are formed from first portions extending from opposite sides of a main body of the article and second portions, respectively, each of the second portions is provided along one side edge with said elastic member, the second portion is placed upon the first portion, and the first portion and the second portion are selectively sealed together in an area between their outer side edges and the elastic member so that the opposite sealing lines are spaced from each other wider at least in a rear area than in a central area.

10 Claims, 8 Drawing Sheets

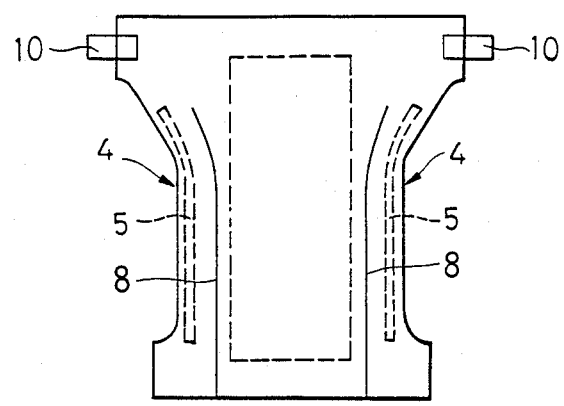
FIG.5
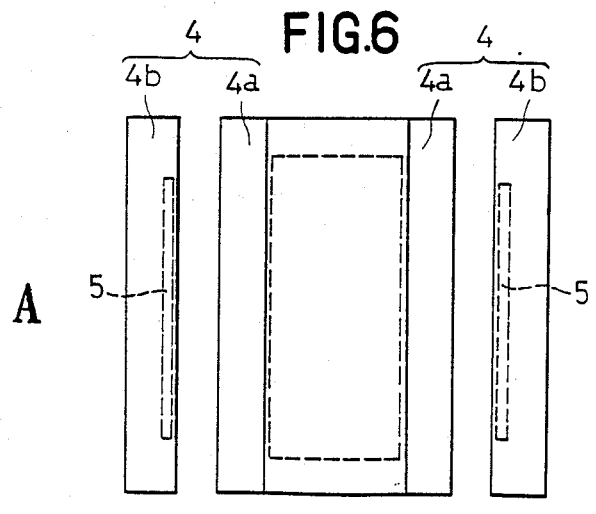
FIG.6
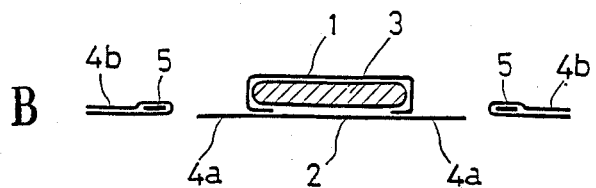

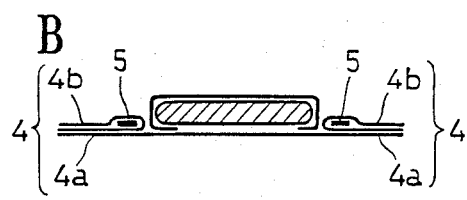

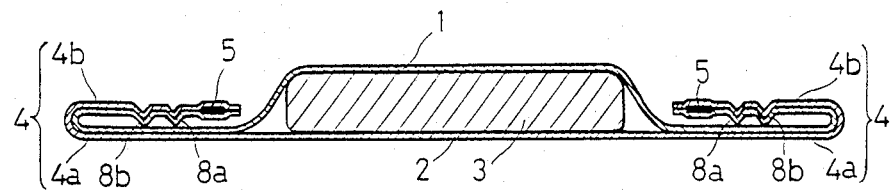
FIG.12
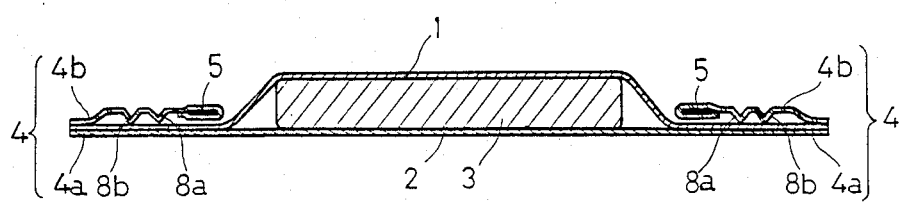
FIG.13
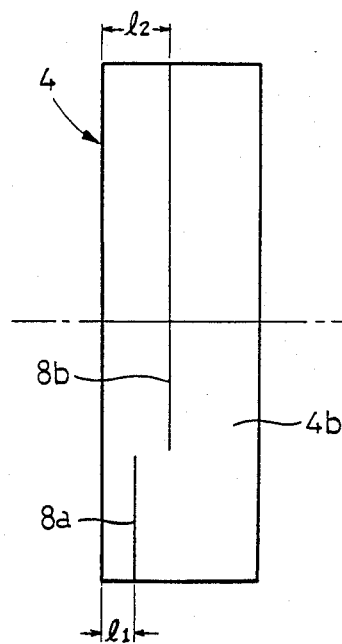
FIG.14
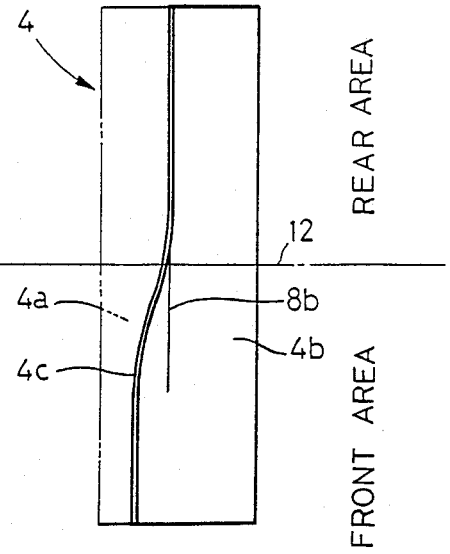
FIG.14-A

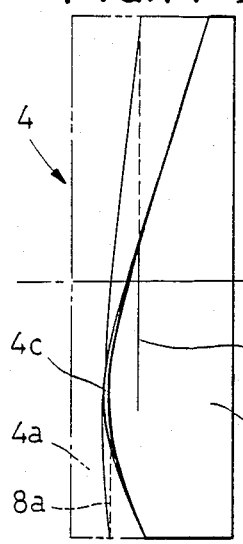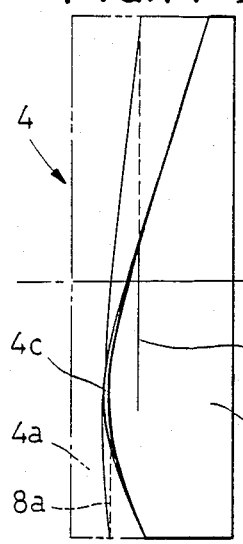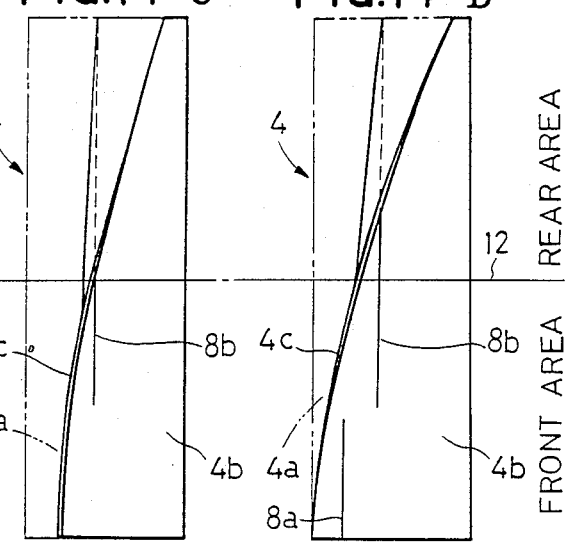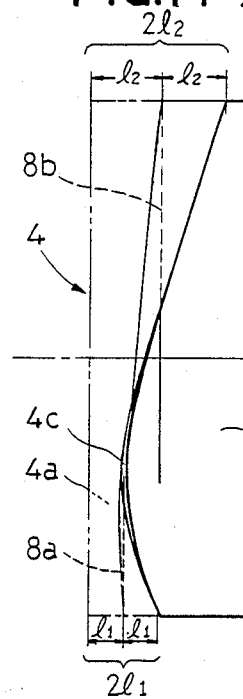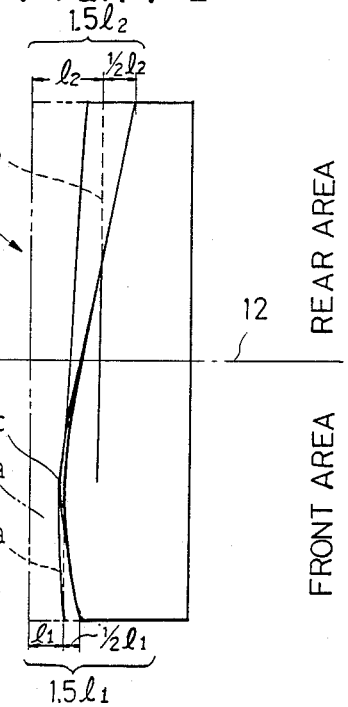

FIG.15  FIG.16
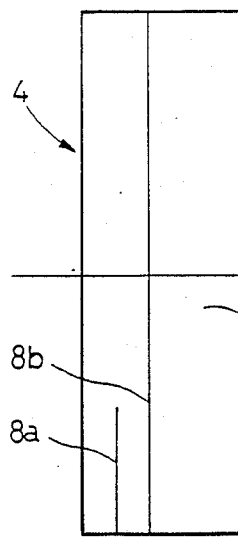
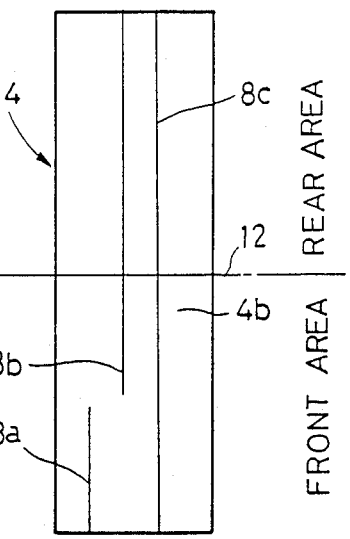
FIG.17  FIG.17-A  FIG.17-B
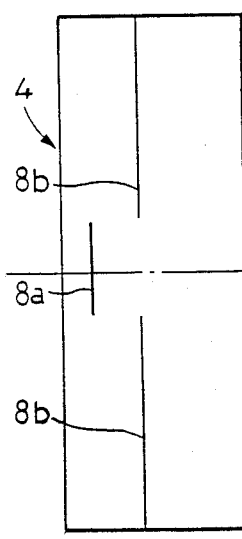
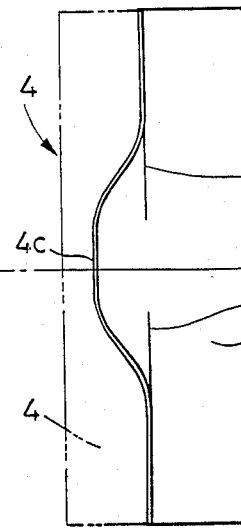
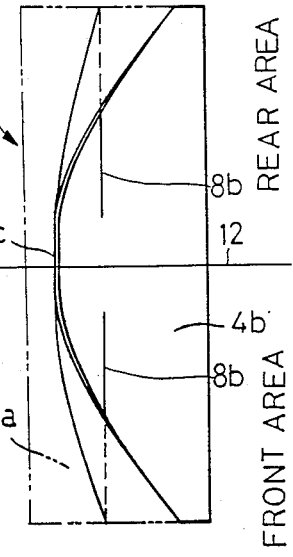

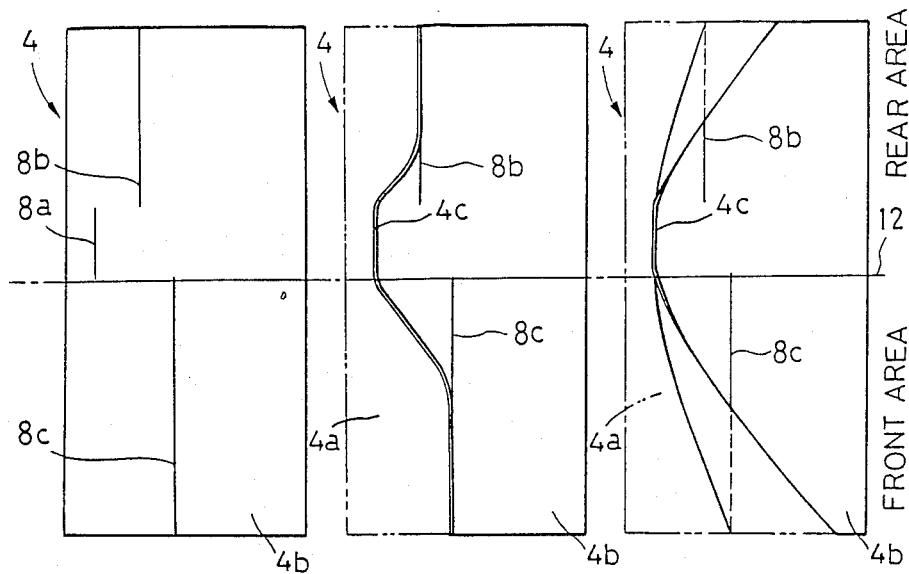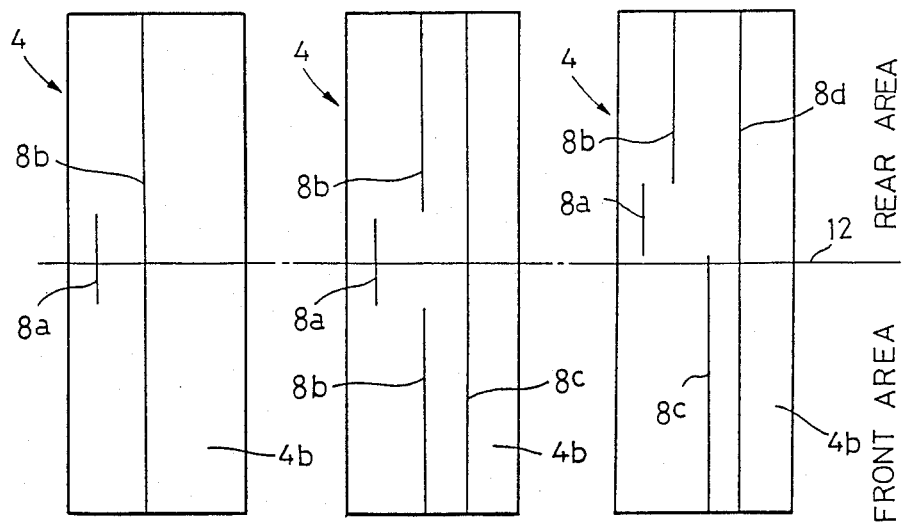

METHOD FOR MAKING WEARABLE ARTICLES

BACKGROUND OF THE INVENTION

The present invention relates to a method for making wearable articles, more particularly to a method for making disposable diaper or disposable diaper cover and especially to a method for incorporation of elastic members to obtain a desired fitness around wearer's legs.

There has already been available the disposable diaper which is provided in opposite side flaps thereof with the elastic members serving to provide a fitness around wearer's legs. In the diaper of this type commonly used in practice, said elastic members usually disposed on opposite sides of the diaper in parallel relationship to each other. To improve said fitness of the diaper around the wearer'legs, it is desired that a distance between the opposite elastic members should be wider in the rear area than in the front area. The diaper constructed to satisfy such requirement is also well known. Furthermore, the diaper of so-called turn-up type has also been used in practice, in which the opposite side flaps provided with the associated elastic members are folded inwardly, then the side flaps are joined at middle portions of their lengths to the upper surface of the topsheet within the area covering the absorbent core so that the opposite elastic members diverge from said joined portions towards the front and rear side of the diaper.

For the diaper of such type which should be mass-produced at a cost as low as possible in view of a commercial competition, it is difficult to establish an economical manufacturing process permitting the distance between the opposite elastic members to be gradually varied. Usually, various components of the diaper and the elastic members are continually fed along the production line of the diaper while said elastic members are fastened to said components with use of adhesive and it is difficult to change the movement direction of said elastic members for each of the individual diapers in a particular unit zone thereof. Even if such difficulty were overcome, such attempt could not meet the requirements for high speed production and, in addition, would possibly cause various troubles. It is for this reason that, as has previously been described, the opposite elastic members for the diaper of such type have conventionally been disposed therein in parallel to each other.

Although said turn-up diaper is relatively easy to produce, the above-mentioned fitness still remains inadequate.

It is a principal object of this invention to provide an improved method for making said diaper allowing said opposite elastic members to be disposed so that the distance therebetween may be selectively varied.

SUMMARY OF THE INVENTION

In a method for making wearable articles such as disposable diaper including side flaps on opposite sides thereof and elastic members incorporated in the respective side flaps to provide an elastic fitness around a wearer's legs, the object as set forth above is achieved, in accordance with the present invention, by an arrangement that said side flaps each consists of a first portion and a second portion provided with each of said elastic members and placed upon said first portion, and said first and second portions are selectively sealed together along their outer side edges.

Conveniently, each of the side flaps comprises the first portion and the second portion placed thereupon, said second portion is provided therein with the elastic member and said first and second portions are sealed together along their outer side edges so that the respective second portions may be developed outwardly along the associated lines of sealing in actual use of the diaper. In this way, in spite of a fact that the opposite elastic members are initially disposed in parallel relationship to each other inside the respective second portion, the distance (i.e., the angle) therebetween will corresponds to that between said lines of sealing which are preset, as said second portions are developed outwardly. In making the diaper, accordingly, it is possible to insure that the distance between the opposite elastic members is wider at least in the rear area than in the crotch area without adoption of the previously mentioned, special, rather complicated means and method to solve this problem. The present invention makes it possible to adopt rather conventional means and method suitable for high speed production and substantially free from occurrence of troubles, by which said opposite elastic members may be initially disposed in parallel relationship to each other.

BRIEF DESCRIPTION OF THE DRAWINGS

FIGS. 1 through 5 sequentially illustrate a process in which a first embodiment of diaper according to the present invention is assembled, in which:

FIG. 1A is a plan view of the diaper as has been provided at opposite sides thereof with elastic members extending in parallel to each other;

FIG. 1B is a schematic cross-section of the same diaper;

FIG. 2A is a plan view of the same diaper with the opposite sides thereof having been folded inwardly;

FIG. 2B is a schematic cross-section of the same diaper in the condition as illustrated by FIG. 2A;

FIG. 3A is a plan view of the same diaper with outer edges along the folding lines having been partially sealed;

FIG. 3B is a schematic cross-section of the same diaper in the condition as illustrated by FIG. 3A;

FIG. 4 is a plan view of the same diaper with areas extending outside the respective sealing lines having been cut off;

FIG. 5 is a plan view of the same diaper with the folded areas having been unfolded outwardly;

FIGS. 6 through 9 sequentially illustrate a process in which a second embodiment of diaper according to the present invention is assembled, in which:

FIG. 6A is a plan view illustrating a main body of diaper formed at opposite sides with side flaps and separate side flap portions provided with elastic members and to be joined to said main body;

FIG. 6B is a schematic cross-section corresponding to FIG. 6A;

FIG. 7A is a plan view of said main body of diaper with said separate side flap portions having been placed on the corresponding side flaps of said main body;

FIG. 7B is a schematic cross-section of the assembly as illustrated by FIG. 7A;

FIG. 8 is a plan view of the same diaper with the opposite side flap areas having been sealed along outer edges thereof;

FIG. 9 is a plan view of the same diaper with the separate side flap portions having been unfolded outwardly;

FIGS. 12 and 13 are sectional views taken along a line XII—XII in FIG. 10;

FIGS. 14, 15, 16, 17, 18 and 19 through 21 are plan views illustrating various manners in which a seal line is arranged in each side flap; and FIGS. 14-A through 14-F, 17-A and 17-B, and 18-A and 18-B are plan views illustrating various shapes into which a free end of the side flap is crooked or curved by the sealing line.

PREFERRED EMBODIMENTS OF THE INVENTION

Figure 1:
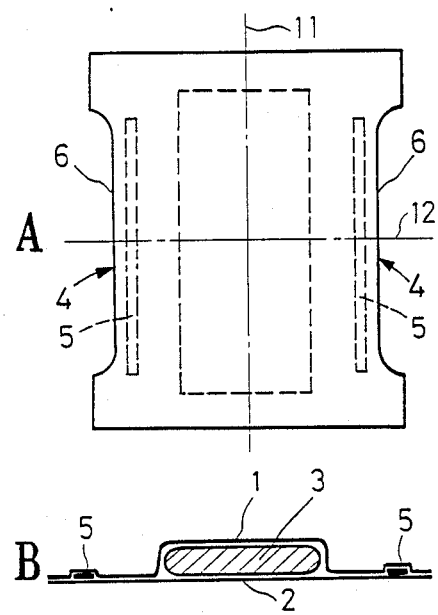
Figure 2:
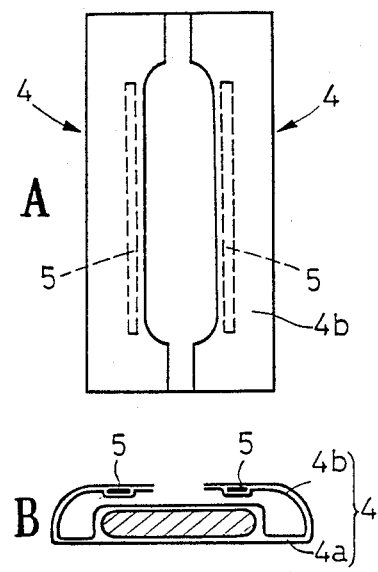
Figure 3:
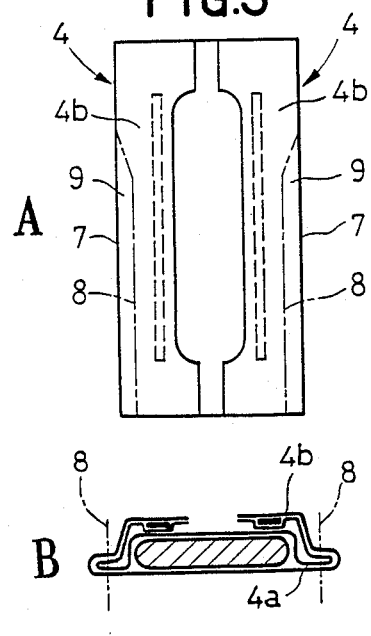
Figure 4:
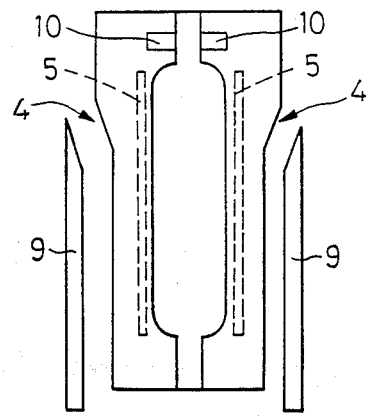
Figure 7:
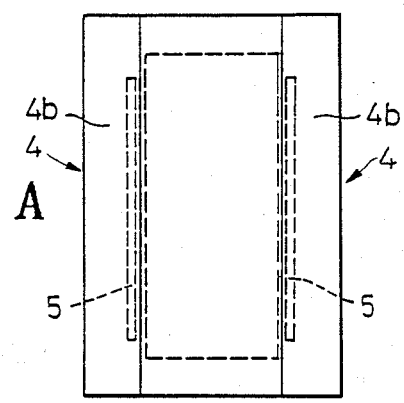

Embodiments of the present invention will be described (taking the case of diaper) in reference with the accompanying drawing.

(A) FIGS. 1A through 5 illustrate a first embodiment of the present invention.

As seen in FIGS. 1A and 1B, an absorbent core 3 is sandwiched between a water-permeable topsheet 1 and a water-impermeable backsheet 2, and elastic members 5 being longitudinally elastic are incorporated in parallel to each other in side flaps 4 respectively formed by portions of said topsheet 1 and backsheet 2 extending outwardly from opposite side edges of said core 3. In this case, the topsheet 1, the backsheet 2 and the core 3 are joined together with adhesive of hot melt type while said portions of the topsheet and the backsheet forming the side flaps 4 are also joined to the elastic members 5 with said adhesive. Opposite sides of the side flaps 4 may be partially cut off so as to form notches 6. It should be understood that the method for making the disposable diaper of such arrangement is well known.

As will be apparent from FIGS. 2A, 2B, 3A and 3B, opposite side flaps 4 of the diaper blank formed in this manner are then folded inwardly so as to define lower first portions 4a and upper second portions 4b overlying said first portions 4a, respectively, then the first and second portions 4a, 4b lying one upon another as a result of folding are respectively sealed in unison along opposite sealing lines 8 so that these sealing lines are spaced from each other wider in a rear area than in a front area of the diaper, and finally portions 9 extending outside the associated sealing lines 8 are cut off to complete formation of the diaper. It should be noted here that said portions 9 sometimes may be left because these portions 9 have no direct relationship with a function of the diaper.

In actual use of the diaper thus completed, the second portions 4b of the respective side flaps 4 may be unfolded outwardly along the associated sealing lines 8, as shown by FIG. 5. In this situation as shown, both a width of the diaper and a distance between the opposite elastic members 5 are larger in the rear area (covering the hip) than in the front area (covering the belly).

(B) FIGS. 6A through 9 illustrate a second embodiment of the present invention.

As seen in FIGS. 6A and 6B, the absorbent core 3 is covered with the water-permeable topsheet 1 except a central area of the lower surface of said core 3 and then this assembly is placed on and joined to a central area of the upper surface of the water-impermeable backsheet 2 integrally therewith. The first portions 4a of the side flaps are formed by the portions of said backsheet extending from the opposite side edges of the core 3 outwardly, respectively. A pair of separately provided water-impermeable sheets in the form of relatively narrow strips is centrally provided with the elastic members 5 being longitudinally elastic and the respective strips are folded along the associated elastic members 5 on themselves, respectively, to form the second portions 4b consisting of the separately provided side flaps.

Figure 8:
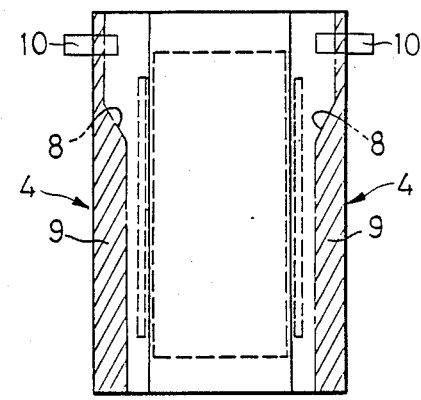

As will be apparent from FIGS. 7A, 7B and 8, starting from these diaper components having respectively been formed in this manner, the respective second portions 4b are placed on the corresponding first portions 4a so that the elastic members 5 extend along the inner sides, respectively, and then these first and second portions 4a, 4b placed one upon another are sealed along the outer side edges integrally with each other in such a manner that the sealing lines 8 extending along opposite inner side edges of the sealed areas are spaced from each other wider in the rear area than the front area of the diaper to complete formation of the diaper. Just as in the case of the first embodiment, the portions 9 extending outside the inner sealing lines 8 may be cut off or left not cut off, as the case demands.

Figure 9:
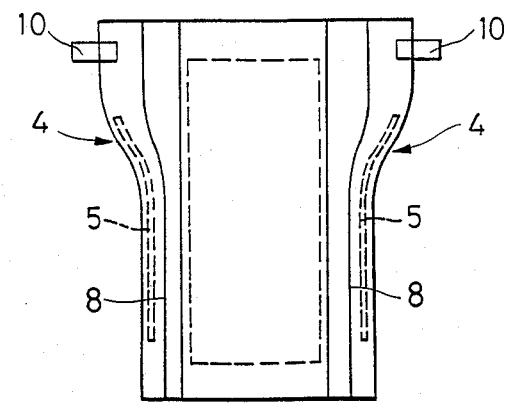

In actual use of the diaper thus completed, the second portions 4b may be unfolded outwardly along the associated inner sealing lines 8, as shown by FIG. 9. In this situation as shown, the width of the diaper as well as the distance between the opposite elastic members 5 are larger in the rear area (covering the hip) than in the front area (covering the belly) of the diaper.

As will be obviously understood from the aforegoing description, the first and second embodiments are substantially identical to each other in view of the objectives of the invention, since the only difference between these two embodiments is that the second portions 4b are folded inwardly in the first embodiment while the separately formed second portions 4b are placed upon and joined to the first portions 4a instead of folding the second portions 4b upon the first portions 4a in the second embodiment.

(C) FIGS. 10 through 21 illustrate a third embodiment of this invention. It should be understood here that this embodiment includes several variants or modifications.

Figure 10:
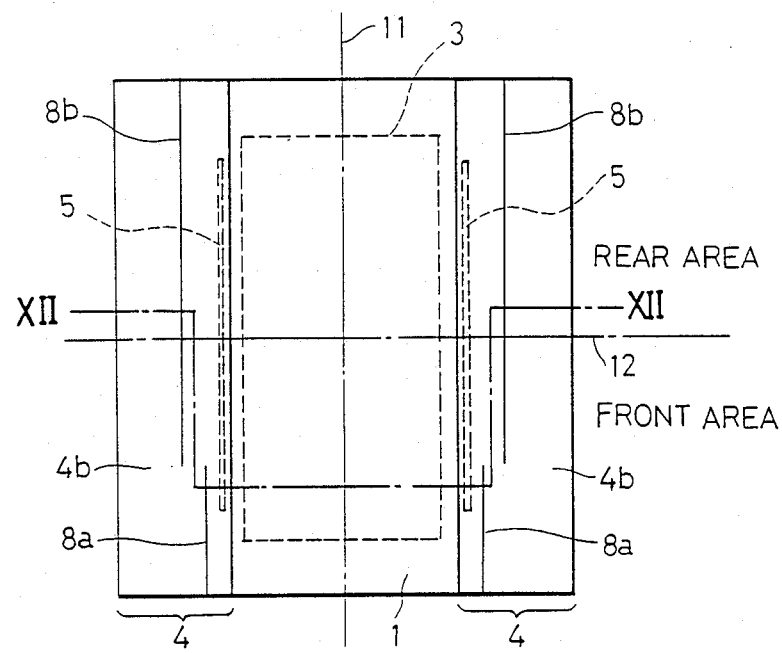
FIG. 10 is a plan view of a third embodiment of diaper constructed in accordance with the present invention as being developed.
Figure 11:
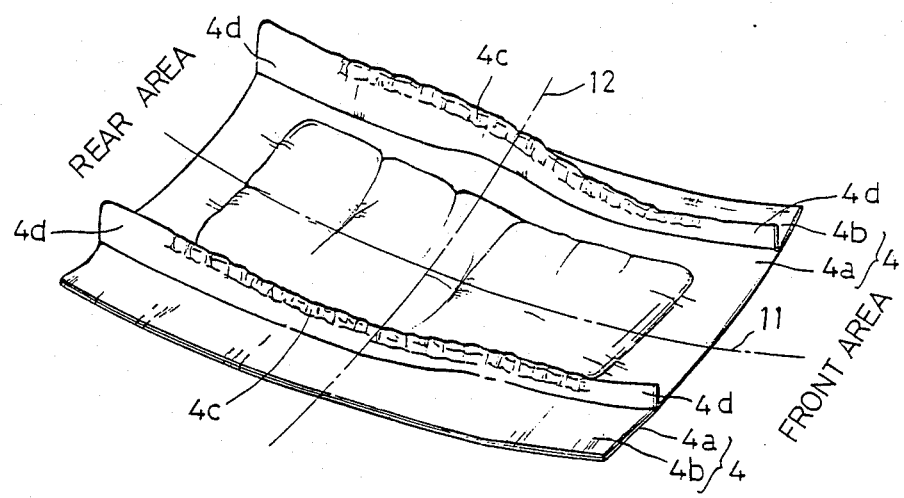
FIG. 11 is a perspective view of the same diaper with the elastic members having been contracted to some degrees.

Referring to FIGS. 10 through 12, the absorbent core 3 is sandwiched between the water-permeable topsheet 1 and the water-impermeable backsheet 2, and the elastic members 5 being longitudinally elastic are incorporated in parallel to each other in the side flaps 4 respectively formed by the portions of said topsheet 1 and backsheet 2 extending outwardly from the opposite side edges of said core 3. In this case, the topsheet 1, the backsheet 2 and the core 3 are joined together with adhesive of hot melt type while said portions of the topsheet and the backsheet forming together the side flaps 4 are also joined to the elastic member 5 with said adhesive. The opposite side flaps 4 are then folded inwardly so as to define the lower first portions 4a and the upper second portions 4b overlying said first portions 4a, respectively, and then the first and second portions 4a, 4b lying one upon another as a result of folding are respectively sealed in unison along inner and outer sealing lines 8a, 8b extending longitudinally of the diaper in said first and second portions 4a, 4b, outside the elastic members provided along the inner side edges of the second portions 4b to form free end portions extending from these sealing lines. The respective inner sealing lines 8a are relatively short and occupy the front halves of the front area, and the outer sealing lines 8b are relatively long and extend from rear ends of the respective inner sealing lines 8a to rear end of the rear area. Although these sealing lines 8a, 8b are exaggeratingly illustrated as if they present V-shaped cross-sections in order to clearly show them on the top surfaces of the side flaps 4, it should be understood that not only the sealing process with use of adhesive but also the welding process never results in such exaggerated shapes.

The complete diaper thus formed has left and right areas which are symmetric in their construction with respect to an imaginary longitudinal central line 11 and, with respect to an imaginary transverse central line 12, front and rear areas.

In the diaper having been formed in the manner as mentioned-above and then sealed along the inner and outer sealing lines 8a, 8b, as seen in FIG. 10, the free end portions 4c of the second portions 4b are raised along the sealing lines 8a, 8b under the contracting effect of the elastic members 5, so far as said elastic members 5 are contracted to some degrees, as seen in FIG. 11. With the free end portions 4c of the respective second portions 4b thus raised, the distance therebetween is narrow in a substantially front half of the front area and is gradually enlarged into the rear area of the diaper.

In FIG. 13, there is illustrated an embodiment in which the second portions 4b are formed separately of the first portions 4a, then placed upon the associated first portions 4a, and these are sealed together along inner and outer sealing lines 8a, 8b. Of course, the present invention is not limited to such an embodiment and may be embodied as illustrated by FIG. 12 in which the respective side flaps 4 are partially folded upon themselves to form the respective second portions 4b.

In the description which follows in connection with FIGS. 14 through 21: (1) Only the side flap 4 in the right area of the diaper as viewed in FIG. 10 will be referred to and no explanation will be given with respect to that in the left area to avoid a repetition; (2) the sealing lines 8a, 8b . . . are meant by those which longitudinally extend in the first portion 4a and the second portion 4b constituting together each of the side flaps 4 and seal these portions together; (3) in embodiments illustrated by FIGS. 14A through 14F, FIGS. 17A and 17B, and FIGS. 18A and 18B, the configurations in which the upper edge of the free end portion 4c of each second portion 4b take when said free end portion 4c is raised along the sealing lines 8a, 8b . . . should be understood as the configurations in the condition that said elastic member 5 disposed along said free end portion 4c has been contracted to some degrees as has previously been described in connection with FIG. 11; (4) in connection with a description on said configurations of the free end portion 4c along its upper edge as viewed from above, double line in each of these figures indicates that an area corresponding to this double line and adjacent thereto is raised substantially in a vertical direction while a single line indicates that an area corresponding to this single line is inclined outwardly over an extent from the ends of said area corresponding to the double line and adjacent thereto to front and/or rear end of this area corresponding to the single line, and completely collapses outwards at said front and rear ends; and (5) expression "front end" and "rear end" of the second portion 4b should be understood to be a portion corresponding to the portion 4d in FIG. 11.

Now, FIG. 14 shows a basic arrangement of the sealing lines in the side flap 4 to insure that the distance between the opposite free end portions 4c in the left and right areas of the diaper (FIG. 10) is relatively narrow in the substantially front half of the front area and is enlarged in the substantially rear half of the front area and the rear area. In this arrangement, in the substantially front half of the side flap 4 in the front area of the diaper there is provided a relatively short inner sealing line 8a and in the substantially rear half of the front area and the rear area there is provided a relatively long continuous outer sealing line 8b. The free end portion 4c formed by such sealing is raised along the sealing lines 8a, 8b, resulting in the upper edge of the free end portion 4c exhibiting a curved configuration substantially as seen in a plan view of FIG. 14A.

With the arrangement as illustrated by FIG. 14A, when the front and rear ends of the free end portion 4c are folded outwards (rightwards as viewed in the figure) and then fastened, the upper edge of the free end portion 4c has a curved configuration substantially as seen in a plan view of FIG. 14B. When only the rear end is folded outwards (rightwards as viewed in the figure) and then fastened, said upper edge has a curved shape substantially as seen in a plan view of FIG. 14C. Finally, when the front end is folded inwards (leftwards as viewed in the figure) and then fastened while the rear end is folded outwards (rightwards as seen in the figure) and the fastened, said upper edge has a curved shape substantially as seen in a plan view of FIG. 14D.

With the arrangement as illustrated by FIG. 14E, the free end portion 4c is folded and fastened over a width $2l_1$, i.e., twice a width $l_1$ extending from the inner side edge of the second portion 4b to the inner sealing line 8a, adjacent the front end, while the free end portion 4c is folded and fastened over a width $2l_2$, i.e., twice a width $l_2$ extending from the inner side edge of the second portion 4b to the outer sealing line 8b, adjacent the rear end. With the arrangement as illustrated by FIG. 14F, the free end portion 4c is folded and fastened over a width $1.5l_1$, i.e., one and half times a width $l_1$ extending from the inner side edge of the free end portion 4c to the inner sealing line 8a, adjacent the front end, while such folding and fastening ocur over a width $1.5l_2$, i.e., one and half times a width $l_2$ extending from the inner side edge of the second portion 4b to the outer sealing line 8b so that the curvature radius for the free end portion 4c in the arrangement of FIG. 14F is larger than that in the arrangement of FIG. 14E.

The arrangement of FIG. 15 differs from the arrangement of FIG. 14 in that the outer sealing line 8b is prolonged to the front end of the front area so as to extend continuously the entire length of the front and rear areas. In the arrangement of FIG. 16, there is provided the outermost sealing line 8c continuously extending over the entire length of the front and rear areas, in addition to the sealing lines 8a, 8b in the arrangement of FIG. 14. Provision of such continuous sealing lines 8b, 8c is suitable for the case in which, as has already been described in connection with the arrangment illustrated by FIG. 13, the second portions 4b are formed separately of the first portions 4a so that the portions 4b are placed upon portions 4a, respectively. Even when the areas of these first and second portions extending outside said sealing lines are not water-tightly joined together, these continuous sealing lines will prevent a quantity of body fluid absorbed in said core 3 from flowing through the interface of the first portions 4a and the second portions 4b to the exterior.

FIG. 17 illustrates a basic arrangement of the sealing lines in the respective side flaps of the diaper to insure that the distance between the laterally opposite free end portions 4c is narrower in a central area with respect to an imaginary transverse central line 12 than in the front and rear areas. In this arrangement, a relatively short inner sealing line 8a is provided so as to cross said imaginary central line 12 at a middle point of said sealing line 8a while relatively long two outer sealing lines 8b are provided in the front and rear areas, respectively. The free end portions 4c thus formed is raised along the sealing lines 8a, 8b and the upper edge thereof has a curved configuration substantially as seen in a plan view of FIG. 17A.

From the condition as shown by FIG. 17A, the front and rear ends of the free end portion 4c are folded outwards and fastened so that the upper edge of the free end portion 4c has a curved configuration substantially as seen in a plan view of FIG. 17B.

FIG. 18 illustrates an arrangement similar to the arrangement of FIG. 17 but which has been slightly modified. In this modified arrangement, a relatively short inner sealing line 8a and a relatively long outer sealing line 8b are provided in the rear area while the longest outermost sealing line 8c is provided in the front area. The free end portions 4c thus formed is raised substantially in a vertical direction along the respective sealing lines 8a, 8b, 8c and the upper edge of the free end portion 4c has a curved configuration substantially as seen in a plan view of FIG. 18A.

From the situation as illustrated by FIG. 18A, the front and rear ends of the free end portion 4c are folded outwards and fastened so that said upper edge of the free end portion 4c has a curved configuration substantially as seen in a plan view of FIG. 18B.

In an arrangement of FIG. 19, the pair of the outer sealing lines 8b in the arrangement of FIG. 17 are made continuous with each other to form a single continuous sealing line. FIG. 20 illustrates an arrangement in which there is provided, in addition to the sealing lines 8a, 8b, the outermost sealing line 8c continuously extending over the entire length of the front and rear areas. Finally, FIG. 21 illustrates an arrangement in which there is provided, in addition to the sealing lines 8a, 8b, 8c in the arrangement of FIG. 18, the outermost sealing line 8d extending over the entire length of the front and rear areas. It is for the same reason as has been mentioned in connection with FIGS. 15 and 16 that there is provided such continuous sealing line 8b, 8c or 8d extending over the entire length of the front and rear areas.

As will be understood from the various arrangements which have been briefly explained above in reference with the respective figures, it is essential for this invention that there should be provided at least the inner and outer sealing lines 8a, 8b to join the first portion 4a and the second portion 4b constituting each side flaps 4. It is also essential that the distance between the outer edge of the core 3 and the free end portion 4c should be relatively large in the area containing no inner sealing line 8a interposed between the inner edge of the second portion 4b and the outer sealing line 8b as well as the imaginary extension thereof. Furthermore, provision of at least the inner and outer sealing lines 8a, 8b allows desired elastic lines to be at least partially formed on the respective free end portions 4c under the action of the respective elastic members 5. Additionally, factors such as position, angle and orientation at which each elastic line is bent or curved can be determined by properly selecting the lengths and the spacing of at least the inner and outer sealing lines 8a, 8b, whether the free end portion 4c is folded inwards and outwards and fastened or not, a combination of folding in/out, and full or partial fastening of the folded portions (FIGS. 14E and 14F).

It should be noted here that the desired joining may occur by means of a plurality of sealing lines (inclusive of short and long sealing lines or a combination thereof) or a wide band-like sealing so far as it concerns the area extending outside the outer sealing line 8b in FIGS. 14, 15, 17 and 19 or the outermost sealing lines 8c, 8d in FIGS. 16, 18, 20 and 21. Such manner of joining is preferred particularly for the case in which the second portions 4b are formed separately of the first portions 4a so as to be then placed upon the latters, respectively, as shown by FIG. 13. The sealing lines 8a, 8b . . . may be provided as chain lines (i.e., intermittent lines) so far as the above-mentioned function is performed.

The topsheet 1 may be of non-woven fabric or porous plastic film, the backsheet 2 may preferably of air-permeable palstic film or laminate sheet of said film and non-woven fabric, the core 3 may be primarily of fluffy pulp, preferably of this fluffy pulp mixed with highly absorptive polymer particles, and the second portion 4b according to the second embodiment may be of air-permeable palstic film, laminate sheet of such film and non-woven fabric or air-permeable non-woven fabric treated with suitable repellent.

The second portions 4b are raised under a contracting effect of the respective elastic members 5 on the line 8 along which the second portions 4b are sealed together with the associated first portions 4a and apt to collapse inwards in use of the diaper. Accordingly, in addition to or in conjunction with the effect of the present invention as mentioned above, there is provided another effect of close fitness around wearer's legs. It will be obvious that the rear or hip area of the diaper is provided on opposite sides with tape fasteners such as 10 (see FIGS. 4, 5, 8 and 9).

What is claimed is:

1. A method for making a wearable absorbent article that includes:
  (1) a liquid absorbent core disposed centrally between a liquid-permeable top sheet and a liquid-impermeable back sheet so that the overall article has a front area, a central area, and a rear area,
  (2) side flaps disposed on opposite sides of the centerline (11) of said absorbent core and extending between said front, central, and rear areas, and
  (3) an elongated elastic member associated with each of said side flaps which will establish elastic lines in each of said side flaps to thereby provide an elastic fitness around a wearer's legs,
said method comprising the steps of
  (a) forming each of said side flaps (4) from a combination of a first portion (4a) having an outer side and a second portion (4b) having both inner and outer sides,
  (b) including an elongated elastic member (5) within each second portion (4b) generally adjacent the inner side thereof,
  (c) disposing each second portion (4b) in an overlying relationship with each first portion (4a) so that the inner side of each second portion (4b) is positioned inwardly of the outer side of each first portion (4a), and (d) joining each second portion (4b) to each first portion (4a) along a juncture line that extends the full length of the article and which includes at least two longitudinally extending and laterally separated sealing lines (8a and 8b), (i) both of said sealing lines being located within the area that extends between the elastic member (5), and the outer sides of said first and second portions (4a, 4b), (ii) both of said sealing lines being in a parallel relationship to the longitudinal centerline (11) of said absorbent core, and (iii) each of said sealing lines being laterally offset from the longitudinal centerline (11) of said absorbent core (3) by different distances, the longitudinally extending sealing line (8b) that is closer to the rear area of the article being laterally offset from the longitudinal centerline (11) of said absorbent core (3) a greater distance than the other longitudinally extending sealing line (8a), and said other longitudinally extending sealing line (8a) extending less than the entire length of each side flap (4), wherein the juncture line established by said sealing step (d) permits the inner side of said second portion (4b) to be folded away from said centerline (11), so that said inner side of said second portion (4b) will not be parallel to said centerline (11) along at least a portion of its length.

2. A method according to claim 1 wherein each second portion (4b) is obtained by folding the outer portions of said side flaps (4) inwardly.

3. A method according to claim 1 wherein each second portion (4b) is separately formed and then joined to a first portion (4a).

4. A method according to claim 1 wherein the free end portions of said second portions (4b) formed as a result of said sealing step (d) each contain an elastic member (5) that extends from the front to the rear of said absorbent article along a path that is not parallel to the centerline (11).

5. A method according to claim 1 wherein the free end portions of said second portion (4b) formed as a result of said sealing step (d) are wider at the rear area of the article than in the front area of the article.

6. A method according to claim 1 wherein after step (d) the rear end of the second portion (4b) is folded outwards and fastened to itself.

7. A method according to claim 1 wherein after step (d) the front end of the second portion (4b) is folded outwards and fastened to itself.

8. A method according to claim 1 wherein after step (d) both the front and rear ends of said second portion (4b) are folded outwards and fastened to itself.

9. A method according to claim 1 wherein after step (d) the front end of said second portion (4b) is folded inwards and fastened to itself and the rear end of said second portion (4b) is folded outwards and fastened to itself.

10. A method for making a wearable absorbent article that includes:

(1) a liquid absorbent core disposed centrally between a liquid-permeable top sheet and a liquid-impermeable back sheet so that the overall article has a front area, a central area, and a rear area, (2) side flaps disposed on opposite sides of the centerline (11) of said absorbent core and extending between said front, central, and rear areas, and (3) an elongated elastic member associated with each of said side flaps which will establish elastic lines in each of said side flaps to thereby provide an elastic fitness around a wearer's legs, said method comprising the steps of (a) forming each of said side flaps (4) from a combination of a first portion (4a) having an outer side and a second portion (4b) having both inner and outer sides, (b) including an elongated elastic member (5) within each second portion (4b) generally adjacent the inner side thereof, (c) disposing each second portion (4b) in an overlying relationship with each first portion (4a) so that the inner side of said second portion (4b) is positioned inwardly of the outer side of each first portion (4a), and (d) joining each second portion (4b) to each first portion (4a) along a flap fold line that extends the full length of the article and which includes at least two longitudinally extending and laterally separated juncture lines:

(i) both of said at least two juncture lines being located laterally and outwardly of said elastic member (5), and (ii) both of said at least two juncture lines being disposed in a parallel relationship to the longitudinal centerline (11) of said absorbent core (3), and (iii) each of said at least two juncture lines being laterally offset from the longitudinal centerline (11) of said absorbent core (3) by different distances, the longitudinally extending juncture line that is closer to the rear area of the absorbent article being laterally offset from the longitudinal centerline (11) of said absorbent core (3) a greater distance than the other longitudinally extending juncture line, and said other longitudinally extending juncture line extending less than the entire length of each side flap (4).

wherein said joining step (d) establishes an elongated flap fold line that includes said juncture lines and about which said inner side of said second portion (4b) has the freedom to be folded away from said centerline (11), said fold line not being parallel to said centerline (11) along at least a portion of its length.

* * * * *